(12) United States Patent
Lu

(10) Patent No.: US 6,953,474 B2
(45) Date of Patent: Oct. 11, 2005

(54) MULTIFUNCTIONAL COOL AND HOT COMPRESS BAG

(76) Inventor: Nan Chin Lu, 235 Chung-Ho Box 8-24, Taipei (TW)

(*) Notice: Subject to any disclaimer, the term of this patent is extended or adjusted under 35 U.S.C. 154(b) by 93 days.

(21) Appl. No.: 10/351,087

(22) Filed: Jan. 27, 2003

(65) Prior Publication Data

US 2004/0147991 A1 Jul. 29, 2004

(51) Int. Cl.$^7$ .................................................. A61F 7/00
(52) U.S. Cl. .......................... 607/114; 607/96; 607/108
(58) Field of Search ................................. 607/114, 108, 607/96; 62/530, 4; 601/55, 56, 148, 149, 154; 206/219

(56) References Cited

U.S. PATENT DOCUMENTS 3,913,559 A * 10/1975 Dandliker .............. 126/263.07
4,381,025 A * 4/1983 Schooley .................... 607/112
6,119,474 A * 9/2000 Augustine et al. ......... 62/259.3

* cited by examiner

*Primary Examiner*—Beverly M. Flanagan
*Assistant Examiner*—Matthew J. Kasztejna (57) ABSTRACT

A multifunctional cool and hot compress comprises two first internal layers. Edges of the two first internal layers being sealed by pressing. An inner space is formed by the two first internal layer being filled with chemical substance. Two second internal layers encloses the two first internal layers. One outer layer surrounding the second internal layers. A press portion is formed by compressing the first internal layers. Moreover, the materials of the outer layer are water-proof rubber and cotton cloth. The water-proof rubber is as an internal layer and the cotton cloth is as an outer layer. The second internal layers are also compressed at the press portion. A through hole is formed on the press portion.

1 Claim, 8 Drawing Sheets

MULTIFUNCTIONAL COOL AND HOT COMPRESS BAG

FIELD OF THE INVENTION

The present invention relates to bags, and particularly to a multifunctional cool and hot compress bag which has a press portion at the center of the bag so as to prevent the cool and hot compress bag from breaking out.

BACKGROUND OF THE INVENTION

Prior art cool and hot compress bag serves to provide heat to the user or take heat from the body of the user. The prior art hot and cool compress bag comprises at least one chemical substance, and two first internal layers. Moreover, the multifunctional hot and cool compress bag can further comprise two second internal layers, two outer layers and a sealed edge.

The chemical substance is material which can retain a temperature in a long time period. The chemical substance may be the mixer of the glue-like material, such as water, sodium, acids, cellulose, pigments, etc.

The two first internal layers can be PE or PP materials or are made with material which is meltable. Edges of the two first internal layers are firstly coupled. Then the edges of the two first internal layers are sealed by pressing so as to formed as a bag. An internal of the two first internal layers is formed with a hollow space for receiving the chemical substance.

The two second internal layers a re made of nylon or are made of material which is difficult to break. The two second internal layers are integrally adhered to outer surfaces of the two first internal layers by pressing.

The two outer layers are made of water-proof rubber or cotton cloth. The sealed edge encloses the stacked structure of the first internal layer, second internal layer and the outer layer. When a bag formed by above prior art structure is placed in a microwave oven, and when the heating time is too long so that the power or temperature is improper, the internal pressure of the bag will increase. The bag will expand continuously so that the first internal layers and the second internal layers will break out.

SUMMARY OF THE INVENTION

Accordingly, the primary object of the present invention is to provide a multifunctional cool and hot compress bag. The bag comprises two first internal layers. Edges of the two first internal layers are firstly aligned. Then edges of the two first internal layers are sealed by pressing. An inner space formed by the two first internal layers is filled with chemical substance. Two second internal layers encloses the two first internal layers. One outer layer surrounds the second internal layers. A press portion is formed by compressing the first internal layers.

Another object of the present invention is to provide a multifunctional cool and hot compress bag, wherein the materials of the outer layer are water-proof rubber and cotton cloth.

A further object of the present invention is to provide a multifunctional cool and hot compress bag, wherein a water-proof rubber is used as an internal layer and a layer of cotton cloth is used as an outer layer. The second internal layers are also compressed at the press portion so as to form the compound press portion with the first internal layer.

The various objects and advantages of the present invention will be more readily understood from the following detailed description when read in conjunction with the appended drawing.

BRIEF DESCRIPTION OF THE PREFERRED EMBODIMENTS

Figure 1:
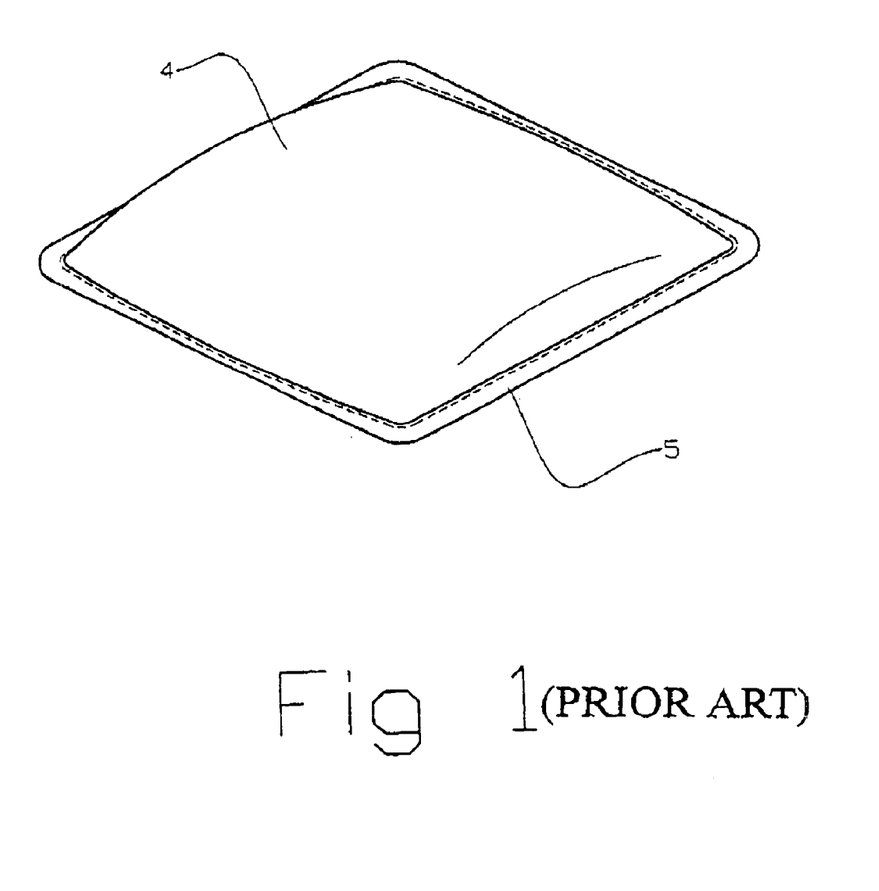
FIG. 1 is a perspective view of a prior art cool and hot compress bag.
Figure 2:
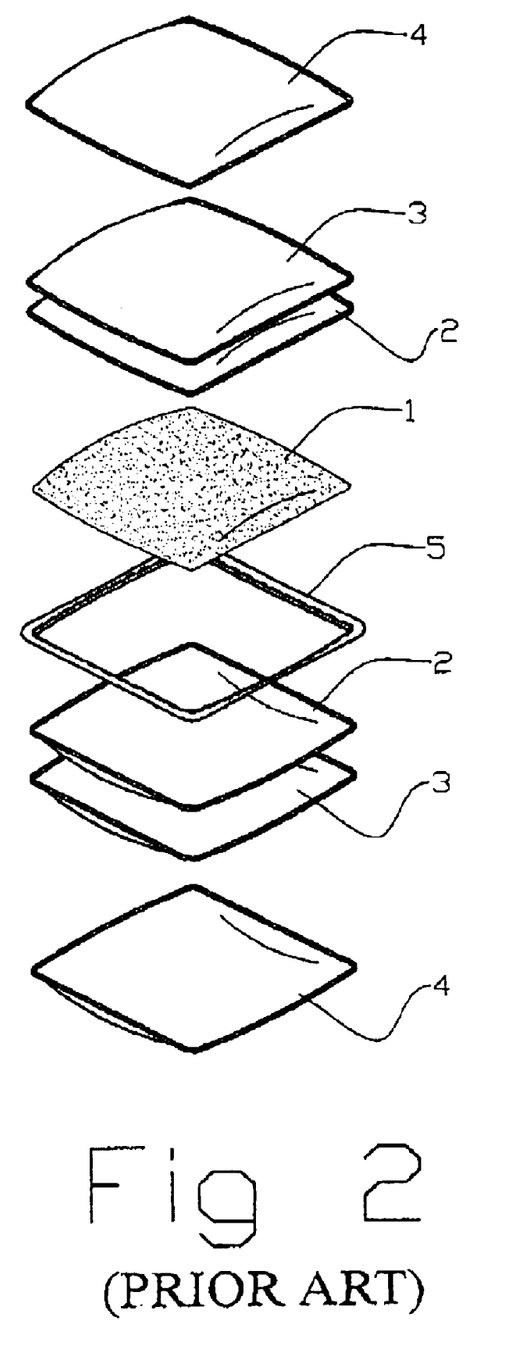
FIG. 2 is an exploded perspective view of the prior art cool and hot compress bag.
Figure 3:
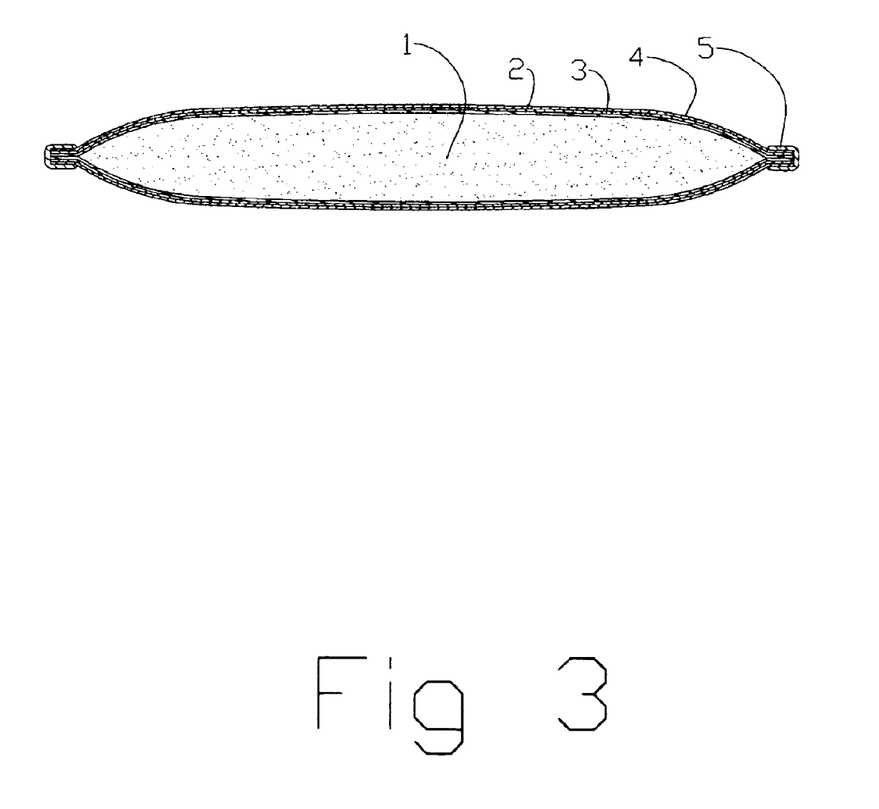
FIG. 3 is a cross sectional view of the cool and hot compress bag of the present invention.
Figure 4:
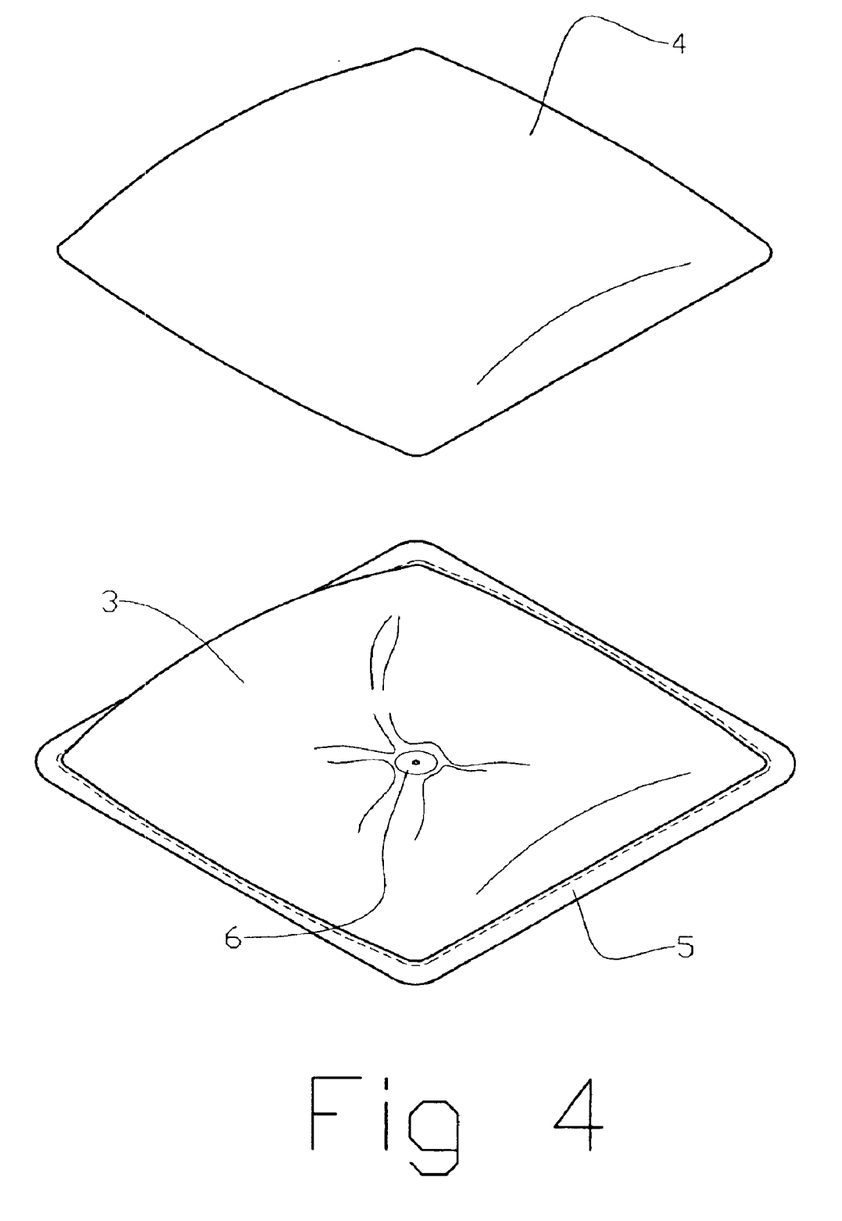
FIG. 4 is a partial exploded perspective view of the cool and hot compress bag of the present invention.
Figure 5:
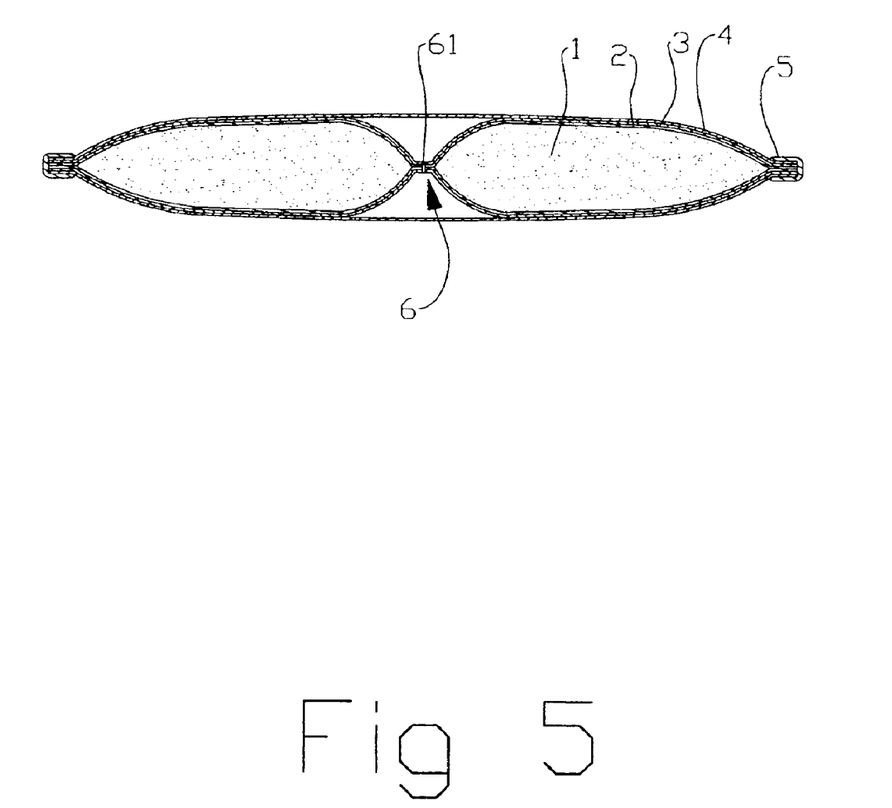
FIG. 5 is a cross sectional view of the cool and hot compress bag of the present invention.

Referring to FIGS. 1, 2 and 3, the multifunctional hot and cool compress bag of the present invention is illustrated. The multifunctional hot and cool compress bag comprises at least one chemical substance 1, and two first internal layers 2. Moreover, the multifunctional hot and cool compress bag can further comprise two second internal layers 3, two outer layers 4 and a sealed edge 5.

The chemical substance 1 is material which can retain a temperature in a long time period. The chemical substance 1 may be the mixer of the glue-like material, such as water, sodium, acids, cellulose, pigments, etc.

The two first internal layers 2 can be PE or PP materials or are made with material which is meltable. Edges of the two first internal layers 2 are firstly coupled. Then the edges of the two first internal layers 2 are sealed by pressing so as to formed as a bag. An internal of the two first internal layers 2 is formed with a hollow space for receiving the chemical substance 1.

The two second internal layers 3 are made of nylon or are made of material which is difficult to break. The two second internal layers 3 are integrally adhered to outer surfaces of the two first internal layers 2 by pressing.

The two outer layers 4 are made of water-proof rubber or cotton cloth.

The sealed edge 5 encloses the stacked structure of the first internal layer 2, second internal layer 3 and the outer layer 4.

Referring to FIG. 3, when a bag formed by above prior art structure is placed in a microwave oven, and when the heating time is too long so that the power or temperature is improper, the internal pressure of the bag will increase. The bag will expand continuously so that the first internal layers 2 and the second internal layers 3 will break out.

Figure 6:
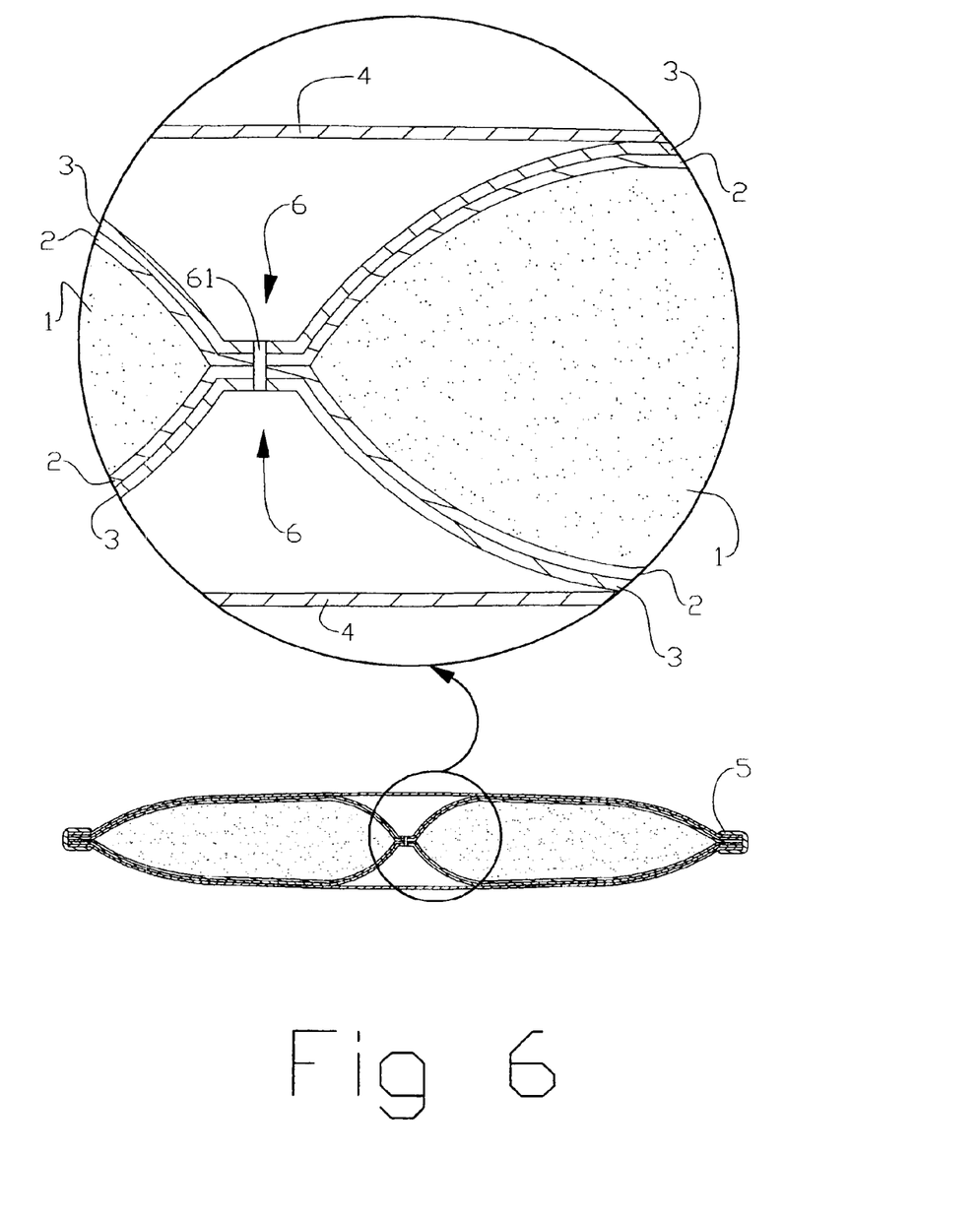
FIG. 6 is an enlarged cross sectional view showing the press portion of the cool and hot compress bag of the present invention.
Figure 7:
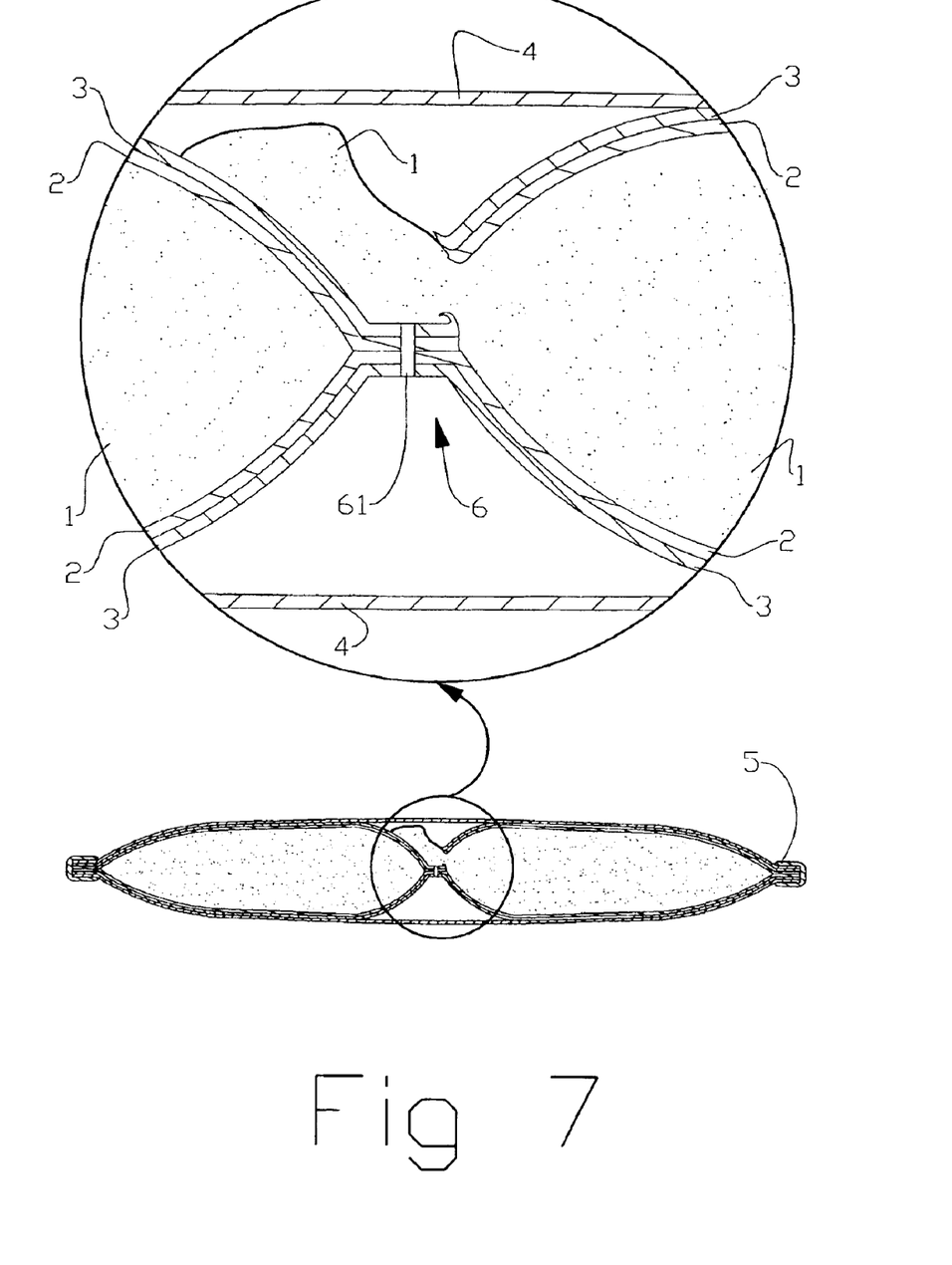
FIG. 7 is a schematic view showing that the cool and hot compress bag of the present invention breaking out as it is heated for a long time period.

To improve the above said defect, a center of a space formed by the first internal layers 2 (and second internal layers 3) is compressed to be formed with a press portion 6. Thereby, when the internal pressure is too large to be tolerated by the bag, as shown in FIG. 6, the bag will break out from a portion illustrated in FIG. 7. Then the chemical substance 1 will flow out in the spaced enclosed by the outer layer 4, instead of flowing out from the whole the cool and hot compress bag.

Moreover, the press portion 6 has the effect of preventing the bag from breaking out so as to provide a safe use to the user.

Figure 8:
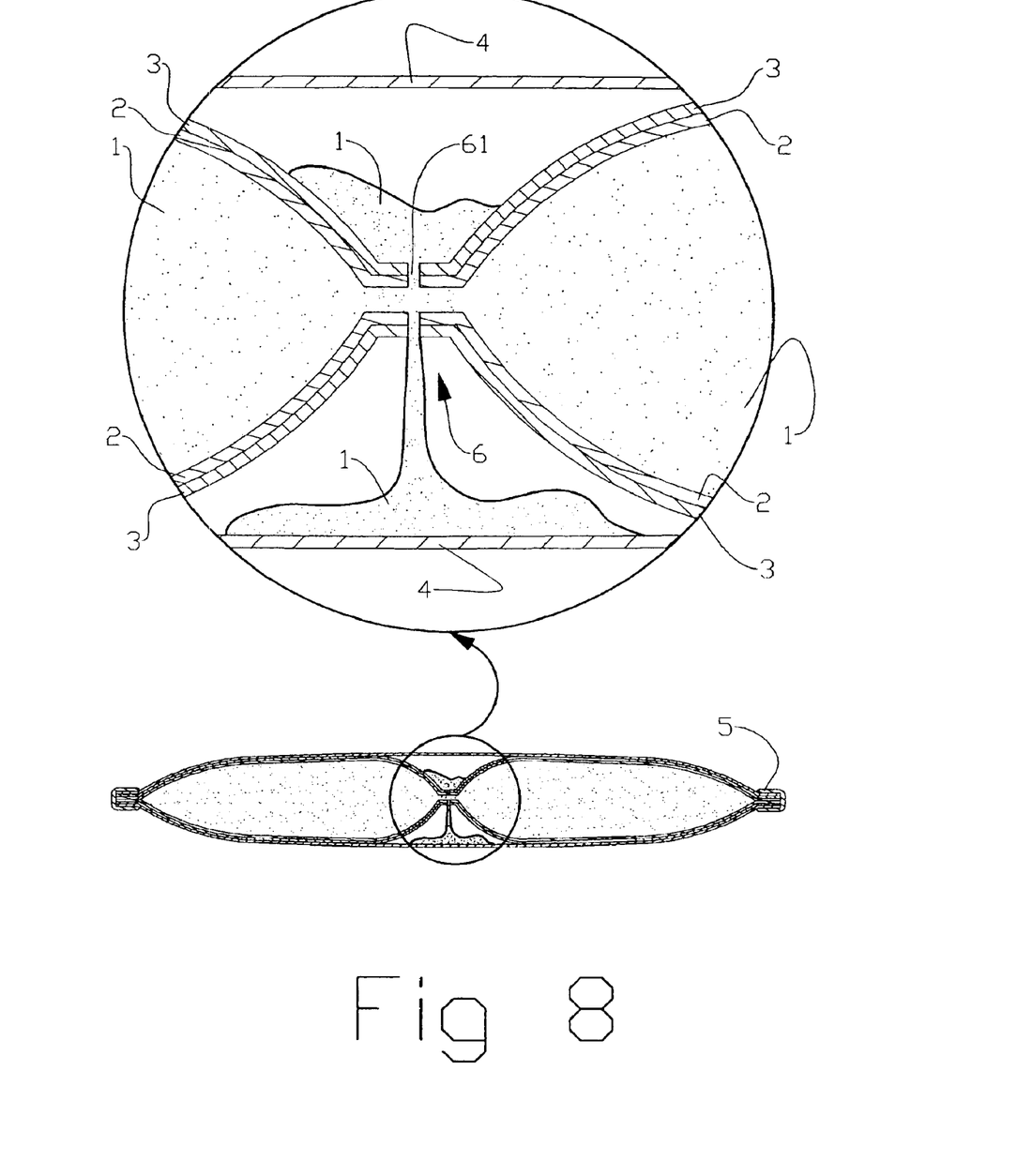
FIG. 8 is a schematic view showing that the chemical substance flows out from the press portion of the cool and hot compress bag of the present invention.

In another embodiment, the press portion 6 can be installed with a through hole 61 (referring to FIG. 6). In general, the through hole 61 has no function. However, once the internal pressure within the bag is too large, so that the press portion is expanded, as shown in FIG. 8, the chemical substance 1 with the first internal layers 2 will flow out from the through hole 61 so as to prevent the bag from breaking out.

A further embodiment of the present invention will be described herein.

The materials of the outer layer 4 are water-proof rubber and cotton cloth. The water-proof rubber is as an internal layer and the cotton cloth is as an outer layer. The water-proof rubber is impermeable and the outer surface of the water-proof rubber will not condense water. The cotton cloth has a predetermined width so as to provide an isolation to the skin of the user from being harmed by the cool and hot compress bag. Thereby, the skin of the user will feel easy.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A multifunctional cool and hot compress bag comprising:

two first internal layers; edges of the two first internal layers being sealed; an inner space formed by the two first internal layers being filled with chemical substance;

two second internal layers enclosing the two first internal layers;

one outer layer surrounding the second internal layers;

characterized in that:

only one press portion is formed by compressing the first internal layers so that the space formed by the first internal layer is collapsed to form the press portion; the press portion is compressed at a position approximately at a center portion of the compress bag; and other portion within the first internal layer is not collapsed;

wherein the second internal layers are also compressed at the press portion, wherein a through hole is formed in the press portion, wherein materials of the outer layer are water-proof rubber and cotton cloth; the water-proof rubber is as an internal layer and the cotton cloth is as an outer layer, wherein the chemical substance is at least one of water, sodium, acids, cellulose, and pigments.

* * * * *